(12) United States Patent
Kitaguchi et al.

(10) Patent No.: US 9,061,108 B2
(45) Date of Patent: Jun. 23, 2015

(54) Aβ-REMOVER, Aβ-REMOVING APPARATUS, AND Aβ REMOVAL METHOD

(71) Applicants: Fujita Health University, Toyoake-shi, Aichi (JP); Kaneka Corporation, Osaka-shi, Osaka (JP)

(72) Inventors: Nobuya Kitaguchi, Nagoya (JP); Kazunori Kawaguchi, Nagoya (JP)

(73) Assignees: FUJITA HEALTH UNIVERSITY, Toyoake-shi (JP); KANEKA CORPORATION, Osaka-shi (JP)

( * ) Notice: Subject to any disclaimer, the term of this patent is extended or adjusted under 35 U.S.C. 154(b) by 0 days.

(21) Appl. No.: 14/060,074

(22) Filed: Oct. 22, 2013

(65) Prior Publication Data

US 2014/0042098 A1    Feb. 13, 2014

Related U.S. Application Data

(63) Continuation of application No. 13/166,431, filed on Jun. 22, 2011, which is a continuation-in-part of application No. PCT/JP2009/007051, filed on Dec. 21, 2009.

(30) Foreign Application Priority Data

Dec. 22, 2008   (JP) ................................. 2008-326174

(51) Int. Cl.
*A61M 1/38* (2006.01)
*A61M 1/36* (2006.01)

(52) U.S. Cl.
CPC ..... *A61M 1/3679* (2013.01); *G01N 2333/4709* (2013.01); *G01N 2800/2821* (2013.01)

(58) Field of Classification Search
USPC .......................................................... 436/86
See application file for complete search history.

(56) References Cited

U.S. PATENT DOCUMENTS

| 5,216,127 A * | 6/1993 | Hirai et al. ................... 530/380 |
| 6,551,266 B1 * | 4/2003 | Davis, Jr. ..................... 604/6.09 |
| 2002/0034723 A1 | 3/2002 | Leinenbach et al. |

(Continued)

FOREIGN PATENT DOCUMENTS

| JP | 1-135533 A | 5/1989 |
| JP | 2005-537254 A | 12/2005 |

(Continued)

OTHER PUBLICATIONS

International Search Report of PCT/JP2009/007051, mailing date Feb. 2, 2010.

(Continued)

*Primary Examiner* — Jill Warden
*Assistant Examiner* — Timothy G Kingan
(74) *Attorney, Agent, or Firm* — Westerman, Hattori, Daniels & Adrian, LLP

(57) ABSTRACT

An object is to provide a material capable of removing Aβ from a body fluid efficiently and use of the material, which are developed for the purpose of establishing a therapeutic or preventive method for Alzheimer's disease. Provided is an amyloid β protein remover, containing a carrier made of any one material selected from the group consisting of cellulose, silica, polyvinyl alcohol, and activated carbon, wherein the carrier does not have an alkyl chain on the surface thereof or has an alkyl chain having 1 to 18 carbon atoms on the surface thereof.

10 Claims, 20 Drawing Sheets

(56) References Cited

U.S. PATENT DOCUMENTS

| | | |
|---|---|---|
| 2002/0192632 A1 | 12/2002 | Hei et al. |
| 2003/0150813 A1 | 8/2003 | Hayashi et al. |
| 2007/0026029 A1 | 2/2007 | Mattner et al. |

FOREIGN PATENT DOCUMENTS

| | | | |
|---|---|---|---|
| JP | 2007-504863 A | 3/2007 | |
| JP | 2008-69346 A | 3/2008 | |
| JP | 2008-506665 A | 3/2008 | |
| WO | 2004-004698 A2 | 1/2004 | |
| WO | 2005-025651 A1 | 3/2005 | |
| WO | WO2005/075507 * | 8/2005 | ............ C07K 14/31 |
| WO | 2006-005706 A2 | 1/2006 | |

OTHER PUBLICATIONS

Akiba et al., "Hemocatharsis Therapy, Clinical Engineering (CE) Technical Series", Nankodo Co., Ltd., Jun. 2004, p. 228.

Bayer et al., "Evaluation of the safety and immunogenicity of synthetic Ab42 (AN1792) in patients with AD", Neurology 2005; 64, pp. 94-101.

Bergamaschini et al., "Peripheral Treatment with Enoxaparin, a low Molecular Weight Heparin, Reduces Plaques and b-Amyloid Accumulation in a Mouse Model of Alzheimer's Disease"; Neurobiol., 24, 2004, pp. 4148-4186.

Holmes et al., "Long-term effects of Aβ42 immunisation in Alzheimer's disease: follow-up of a randomised, placebo-controlled phase I trial", Lancet. Jul. 19, 2008; 372 99634, pp. 216-223.

Motomura et al., "Amyloid b-Protein (1-40) HPM Alzheimer"; Kyoto Medical Journal, vol. 53, No. 1, Jun. 2006, pp. 113-120.

Lemere et al., "Evidence for peripheral clearance of cerebral Aβ protein following chronic, active Aβ immunization in PSAPP mice", Neurobiology of Disease, 14, 2003, pp. 10-18.

Levites et al., "Interacranial Adeno-Associated Virus-Mediated Delivery of Anti-Pan Amyloid b , Amyloid b40, and Amyloid b42 Single-Chain Variable Fragments Attenuates Plaque Pathology in Amyloid Precursor Protein Mice"; The Journal of Neuroscience., Nov. 15, 2006—26(46), pp. 11928-11928.

Matsuoka et al., "Novel Therapeutic Approach for the Treatment of Alzheimer's Disease by Peripheral Administration of Agents with an Affinity to b-Amyloid", The Journal of Neuroscience, Jan. 1, 2003, 23(1): pp. 29-33.

Rubio et al., "Plasma amyloid-β, Aβ1-42, load is reduced by haemodialysis"; Journal of Alzheimer's Disease 10 (2006), pp. 439-443.

Sulowicz et al., "Application of LDL-apheresis and immunoadsorption in kidney diseases", Roczniki Akademii Medycznej w Bialymstoku, vol. 49, 2004, pp. 127-134, cited in U.S. Office Action dated Jul. 24, 2013.

U.S. Final Office Action dated Jul. 24, 2013, issued in related U.S. Appl. No. 13/166,431 (7 pages).

* cited by examiner

Fig. 14

| | Before dialysis (a) | 1-hour dialysis, before Lx (a') | 1-hour dialysis, after Lx (b) | 1-hour dialysis, after dialyzer (c) | After dialysis (a") |
|---|---|---|---|---|---|
| FD001 | 596.03 | 333.65 | 170.17 | 89.54 | 350.1 |

*Fig. 15*

|  | Removal ratio before and after dialysis | Removal ratio before and after Lx column | Removal ratio before and after dialyzer | Decrease ratio after 1 hour-dialysis |
|---|---|---|---|---|
| F0001 | 41.3%<br>(a-a" / a) | 49.0%<br>(a'-b / a') | 47.4%<br>(b-c / b) | 44.0%<br>(a-a' / a) |
| F0002 | 25.0%<br>(a-a" / a) | — | 43.8%<br>(a'-c / a') | 17.5%<br>(a-a' / a) |

Fig. 16

|  | Before dialysis (a) | 1-hour dialysis, before dialyzer (a') | 1-hour dialysis, after dialyzer (c) | After dialysis (a'') |
|---|---|---|---|---|
| FD002 | 527.42 | 435.21 | 244.56 | 395.6 |

Fig. 17

| Aβ1-40 concentration (pg/mL) | Before treatment (a) | 1 hour after initiation of dialysis | | 4 hours after initiation of dialysis | |
|---|---|---|---|---|---|
| | | Lx column inlet (a) | Lx column outlet (b) | Lx column inlet (a) | Lx column outlet (b) |
| Patient A | 606.0 | 372.3 | 206.6 | 292.1 | 148.1 |
| Patient B | 500.1 | 318.4 | 166.6 | 280.4 | 136.5 |
| Aβ1-40 removal ratio (%) | Before and after treatment | Before and after Lx column at 1 hour after initiation of dialysis | | Before and after Lx column at 4 hours after initiation of dialysis | |
| Patient A | 51.8 | 44.5 | | 49.3 | |
| Patient B | 43.9 | 47.7 | | 51.3 | |
| Aβ1-42 concentration (pg/mL) | Before treatment (a) | 1 hour after initiation of dialysis | | 4 hours after initiation of dialysis | |
| | | Lx column inlet (a) | Lx column outlet (b) | Lx column inlet (a) | Lx column outlet (b) |
| Patient A | 51.7 | 33.7 | 23.0 | 29.3 | 16.9 |
| Patient B | 47.9 | 35.3 | 20.6 | 31.4 | 17.6 |
| Aβ1-42 removal ratio (%) | Before and after treatment | Before and after Lx column at 1 hour after initiation of dialysis | | Before and after Lx column at 4 hours after initiation of dialysis | |
| Patient A | 43.3 | 31.8 | | 42.3 | |
| Patient B | 34.4 | 41.6 | | 44.0 | |

Aβ-REMOVER, Aβ-REMOVING APPARATUS, AND Aβ REMOVAL METHOD

CROSS REFERENCE TO RELATED APPLICATIONS

This application is a continuation of U.S. application Ser. No. 13/166,431 filed Jun. 22, 2011, which is a continuation-in-part of international application No. PCT/JP2009/007051, filed Dec. 21, 2009, which claims priority to Japanese application No. 2008-326174, filed Dec. 22, 2008. The contents of these applications are hereby incorporated by reference in their entirety.

FIELD OF THE INVENTION

The present invention relates to an Aβ remover for removing an amyloid β protein (Aβ) from a body fluid. The invention also relates to an Aβ removing apparatus and an Aβ removal system which use the Aβ remover.

BACKGROUND OF THE INVENTION

Alzheimer's disease is cognitive disorder that denatures intracerebral nerve cells due to accumulating an amyloid β protein (hereinafter, abbreviated as "Aβ") in the brain. For the pathogenesis, the most prevailing is the "amyloid hypothesis" such that soluble Aβ strongly inhibits long-term enhancement of memory and Aβ that is coagulated and deposited forms fibrils to thus lead nerve cells to death.

Due to administration of an antibody against Aβ (anti-Aβ antibody) and administration of an Aβ vaccine, deletion of Aβ deposition in the brain as well as improvement in symptoms of cognitive disorder were reported, and possibility that Alzheimer's disease can be treated was shown (Non-patent Document 1). However, administration of an Aβ vaccine caused death for side effects and a clinical trial was thus ceased (Non-patent Document 2); accordingly, the goal to establishing a therapeutic method for Alzheimer's disease is far. On the other hand, development of an anti-Aβ antibody excellent in therapeutic effects has progressed by a number of research groups, but a therapy with an anti-Aβ antibody is expensive and takes over a long period of time, and thus, burden on a patient is severe. In addition, an anti-Aβ antibody has a problem such that its effects are comparatively short, which thus requires repeated administrations. Note that Patent Documents 1 and 2 are shown as prior art documents.

PRIOR ART DOCUMENTS

Patent Documents

Patent Document 1: Japanese Unexamined Patent Application Publication (JP-A) No. 2005-537254
Patent Document 2: JP-A No. 2008-50665

Non-Patent Documents

Non-patent Document 1: Bayer A et al., Neurology 2005; 64: 94-101.
Non-patent Document 2: Holmes C et al.: Lancet. 2008 Jul. 19; 372(9634): 216-23.
Non-patent Document 3: Lemere, C. A. et al.: Nuerobiol. Dis., 14: 10-18, 2003
Non-patent Document 4: Matsuoka Y. et al.: J. Neurosci., 23: 29-33, 2003
Non-patent Document 5: Bergamaschini, L. et al.: J. Neurosci., 24:4148-4186, 2004
Non-patent Document 6: Levites, Y. et al.: J. Neurosci., 26: 11923-11928, 2006
Non-patent Document 7: Kyoto Medical Journal, Vol. 53, No. 1, June, 2006, pp. 113 to 120
Non-patent Document 8: Isabel Rubio et al., Journal of Alzheimer's Disease 10 (2006) 439-443
Non-patent Document 9: CE Technical Series, Hemocatharsis Therapy, Takashi Akiba, Michio Mineshima, p. 228 (Nankodo Co., Ltd.)

SUMMARY OF THE INVENTION

The present inventors repeatedly studied in order to solve the above described problems. Firstly, Aβ adsorption abilities (removal abilities) of existing medical adsorbing materials were evaluated in comparison. As a result, high Aβ adsorption abilities were shown in an adsorbent obtained by fixing a hexadecyl group ($C_{16}$) as a ligand to a carrier made of cellulose beads, an adsorbent obtained by covering a surface of a bead-like activated carbon with a hydrophilic polymer, and an adsorbent obtained by fixing tryptophan as a ligand to a carrier made of a polyvinyl alcohol gel. On the other hand, on the assumption that higher hydrophobicity of the surface is excellent in an adsorption ability of Aβ having higher hydrophobicity, a relationship between a length of an alkyl group (ligand) fixed to a carrier and an Aβ adsorption ability was examined. As a result, contrary to the initial assumption, it was revealed in an experiment using silica as a carrier that as a length of an alkyl group is short (that is, as hydrophobicity is weak), an Aβ adsorption ability is enhanced. After this finding was obtained, in order to confirm whether an Aβ adsorption ability is shown even in a hydrophilic carrier or not, an Aβ adsorption ability of a cellulose bead that is a hydrophilic carrier was examined, an excellent Aβ adsorption ability was shown. Subsequently, usefulness of an adsorbent showing an excellent Aβ adsorption ability was studied in an experimental system modeled after a clinical use (continuously supplying an Aβ solution to an adsorbent column with a pump.) The result was positive, and it was suggested that a clinical application is sufficiently possible. For a further experiment, an extracorporeal circulation system incorporated serially with a column for an adsorbent that has showed an excellent Aβ adsorption ability, and a dialysis apparatus was constructed to try removal of Aβ from blood; as a result, it was shown that the column of the adsorbent enabled efficiently removing Aβ, and an Aβ removal ratio was improved due to using a dialysis apparatus in combination. As described above, as a result of the intensive studies made by the present inventors, they succeeded in finding out a material having a high Aβ adsorption ability. Use of the material makes it possible to efficiently remove Aβ in a body fluid extracorporeally and to realize a therapeutic or preventive method of Alzheimer's disease providing excellent characteristics as shown in (1) to (3) below.

(1) Side effects are less. For example, side effects in an immunotherapy such as activation of T cells hardly occur.

(2) A prompt effect is obtained. A blood Aβ concentration can be decreased in a few hours. Decrease in an intracerebral Aβ concentration with the decrease in the blood Aβ concentration can be expected.

(3) The method can be inexpensively carried out as compared to an immunotherapy, etc.

The present invention is mainly based on the above described findings and results. The present invention is as follows:

[1] An amyloid β protein remover, containing a carrier made of any one material selected from the group consisting of cellulose, silica, polyvinyl alcohol, and activated carbon, wherein the carrier does not have an alkyl chain on the surface thereof or has an alkyl chain having 1 to 22 carbon atoms on the surface thereof.

[2] The amyloid β protein remover according to [1], wherein the material is cellulose or activated carbon.

[3] The amyloid β protein remover according to [1], wherein the material is silica and the alkyl chain is bound to the carrier via a silanol group (SiOH).

[4] The amyloid β protein remover according to [3], wherein the number of carbon atoms is 1 to 5.

[5] The amyloid β protein remover according to [3], wherein the number of carbon atoms is 1 to 2.

[6] The amyloid β protein remover according to [1], wherein the material is silica and the carrier does not have an alkyl chain on the surface thereof.

[7] The amyloid β protein remover according to [1], wherein the material is activated carbon and the surface of the carrier is covered with a hydrophilic polymer.

[8] The amyloid β protein remover according to [7], wherein the hydrophilic polymer is a polymer of methacrylic acid 2-hydroxyethyl ester (pHEMA).

[9] An amyloid β protein removing apparatus, wherein the amyloid β protein remover according to [1] is contained in a container provided with an inlet and an outlet.

[10] The amyloid β protein removing apparatus according to [9], wherein the container is in a shape of a column, and the amyloid β protein remover is filled in the container.

[11] An amyloid β protein removal system, containing the amyloid β protein removing apparatus according to [9], and a pump for supplying a liquid to the amyloid β protein removing apparatus.

[12] The amyloid β protein removal system according to [11], further containing a dialysis apparatus serially connected to the amyloid β protein removing apparatus.

[13] The amyloid β protein remover according to [1], wherein the carrier is made of cellulose and has the alkyl chain on the surface thereof.

[14] The amyloid β protein remover according to [13], wherein the number of carbon atoms is 16 to 22.

[15] The amyloid β protein remover according to [13], wherein the number of carbon atoms is 16.

BRIEF DESCRIPTION OF THE DRAWINGS

These and other objectives and technical advantages of the present invention will be readily apparent from the following description of the preferred exemplary embodiments of the invention in conjunction with the accompanying drawings, in which:

FIG. 14 shows results of the blood purification experiment. An Aβ1-40 concentration at each point in the case where a column filled with Lx (Lixelle) and a dialysis apparatus were used in combination is shown.

FIG. 15 shows results of the blood purification experiment. A removal ratio of Aβ1-40 is shown. The upper shows an Aβ1-40 removal ratio in the case where a column filled with Lx (Lixelle) and a dialysis apparatus were used in combination, and the lower shows an Aβ1-40 removal ratio in the case where a dialysis apparatus was solely used.

FIG. 16 shows results of the blood purification experiment (comparative example). An Aβ1-40 concentration at each point in the case where a dialysis apparatus was solely used is shown.

FIG. 17 shows results of the blood purification experiment (Example 12). Concentrations and removal ratios of Aβ1-40 and Aβ1-42 at each point in the case where a column filled with the sample name Lx and a dialysis apparatus were used in combination are shown.

DETAILED DESCRIPTION OF THE INVENTION

Figure 1:
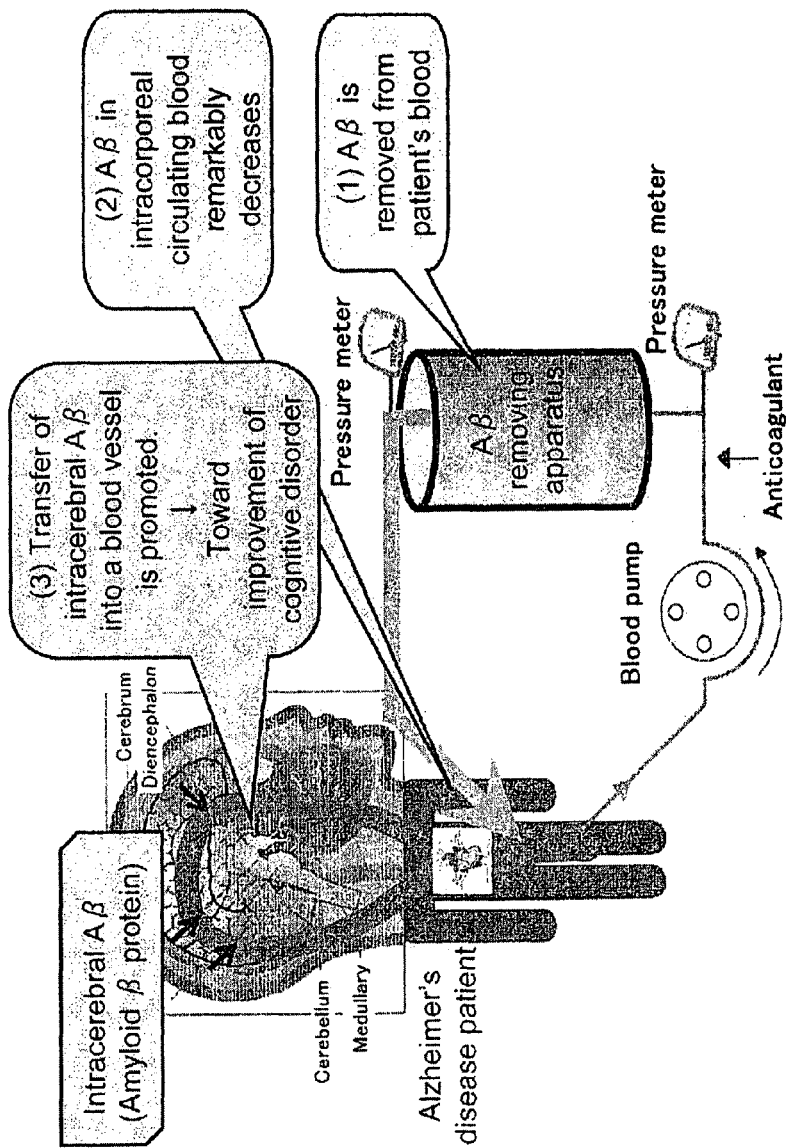
FIG. 1 is a schematic view of an extracorporeal circulation system into which an Aβ removing apparatus is incorporated (one example). In this example, the blood is continuously supplied to an Aβ removing apparatus (column filled with Aβ remover) with a pump to be treated. Aβ in the blood is removed by the Aβ removing apparatus (1). According to the "sink hypothesis", the system enables Aβ in the intracorporeal circulating blood to decrease (2) and promotes transfer of intracerebral Aβ into a blood vessel (3). As a result, improvement in cognitive disorder is attempted.

The first aspect of the present invention relates to an amyloid β protein (Aβ) remover. Aβ is constituted with 40 to 43 amino acids and is produced from a precursor (APP: amyloid β protein precursor) by functions of β and γ secretases. Main molecular species are Aβ1-40 and Aβ1-42. Strong neurotoxicity is recognized in the latter. The "Aβ remover" of the present invention is excellent in adsorption property to Aβ and can remove Aβ from a solution containing Aβ.

Materials of a carrier constituting the Aβ remover of the present invention are cellulose, silica, polyvinyl alcohol or activated carbon. In one embodiment, no alkyl chain exists on the surface of the carrier. In another embodiment, an alkyl chain having 1 to 22 carbon atoms is present on the surface of the carrier.

As shown in examples described later, Lixelle of a cellulose carrier and Hemosorba of an activated carbon carrier showed excellent Aβ adsorption abilities. Based on this fact, a material of a carrier is preferably cellulose or activated carbon.

When an activated carbon is used as a carrier, in order to reduce a reciprocal action with blood cells in treating the whole blood containing the blood cells, the surfaces thereof are preferably covered with a hydrophilic polymer. Kinds of the hydrophilic polymer are not particularly limited. For example, a polymer of methacrylic acid 2-hydroxyethyl ester, polyvinyl pyrrolidone (PVP), polyethylene glycol (PEG), or the like, can be adopted as a hydrophilic polymer.

On the other hand, from the result of an experiment using silica as a carrier, Aβ adsorption abilities were also recognized in both of silica without having an alkyl group on the surface, and silica having an alkyl chain with 2 to 18 carbon atoms on the surface via a silanol group (SiOH). Further, it was found that the shorter a length of an alkyl chain is, the higher an adsorption ability becomes. Based on these findings, in one preferable embodiment of the present invention, a material of a carrier is silica and no alkyl chain exists on the surface of the carrier. In another preferable embodiment, a material of a carrier is silica and an alkyl chain having 2 to 18 carbon atoms is bound to the surface of the carrier via a silanol group. It is preferable that the number of carbon atoms in an alkyl group is less, and the number is preferably 1 to 5, and more preferably 1 to 2.

Further, from the result of an experiment using cellulose as a carrier, it was found that the longer a length of an alkyl chain is, the higher an adsorption ability becomes. Based on these findings, in one preferable embodiment of the present invention, a material of a carrier is cellulose and an alkyl chain having 2 to 22 carbon atoms is bound to the surface of the carrier. The number of carbon atoms in an alkyl chain is preferably 16 to 22.

In Aβ removal from actual patient's blood, it is preferred to select an Aβ remover also in consideration of evaluations of blood compatibility such as low antithrombogenicity and low complement activation.

A commercially available medical adsorbing material can be used as a carrier constituting the Aβ remover of the present invention. Examples of a preferable medical adsorbing material include Lixelle (trade name: KANEKA CORPORATION), Immusorba (trade name: Asahi Kasei Kuraray Medical Co., Ltd.), and Hemosorba (trade name: Asahi Kasei Kuraray Medical Co., Ltd.). Lixelle has a structure in which a hexadecyl group is bound to the surface of cellulose beads as a ligand. Immusorba is a material having a polyvinyl alcohol gel as a carrier and tryprophane (Immusorba TR) or phenylalanine (Immusorba PH) as a ligand. Hemosorba is a carrier made of petroleum pitch-based bead-like activated carbon, and the surface thereof is covered with a polymer of methacrylic acid 2-hydroxyethyl ester.

A shape of the Aβ adsorbing material of the present invention is not particularly limited. Examples of the shape include granule, gel, porous body, and hollow fiber, which are fixation materials to a surface. An average particle size in the case of a granular shape is, for example, 1 μm to 5 mm, preferably 30 μm to 3 mm, and more preferably 50 μm to 800 μm.

The Aβ adsorbing material of the present invention is utilized for removing Aβ in a body fluid. That is, use of the Aβ adsorbing material of the present invention is removal of Aβ in a body fluid. Herein, "removal" means removing at least a part of Aβ that is present in a body fluid, and includes both partial removal and complete removal.

For a treatment in the case of removing Aβ using the Aβ adsorbing material of the present invention, either of a batch treatment or a continuous treatment may be used. In the case of the latter, for example, an Aβ remover is contained in a container provided with an inlet and an outlet to form an Aβ removing apparatus, and a body fluid is passed through the Aβ removing apparatus. The container is typically in a column shape, and is not limited thereto. According to a column filled with an Aβ remover, a system excellent in operation ability can be constructed. The shape of the column is desirably in a shape such that the blood flows uniformly and with less pressure resistance. An elongated shape is preferable in order to increase an Aβ removal ratio between the inlet and the outlet of the column, and on the other hand, a thick and short shape is preferable in order to decrease pressure resistance; therefore, a suitable shape may be selected depending on a size (particulate diameter) of an Aβ remover.

As shown in FIG. 1, when an Aβ removing apparatus and a pump are used in combination, an Aβ removal system (extracorporeal circulation system) can be constructed. The pump is for supplying a body fluid to the Aβ removing apparatus continuously, and the structure thereof, etc are not particularly limited as long as the function is provided. For example, a pump for a blood purification apparatus, a pump for a dialysis treatment, a perista pump (roller pump), and the like can be used.

Two or more Aβ removing apparatuses are prepared and these may be serially connected. In this case, two or more Aβ removing apparatuses filled with different Aβ removers had better be used in combination. For example, when an Aβ removing apparatus filled with an Aβ remover excellent in an Aβ1-40 adsorption ratio and an Aβ removing apparatus filled with an Aβ remover excellent in an Aβ1-42 adsorption ratio are used in combination, a system capable of efficiently removing both Aβ1-40 and Aβ1-42 can be constructed. Alternatively, it is also useful to use a remover having a high removal ratio of an Aβ oligomer obtained by molecular association of plural Aβ and an Aβ remover having a high removal ratio of an Aβ monomer.

A liquid treated by the Aβ removal system of the present invention is a body fluid. Specifically, blood (e.g., peripheral blood), cerebrospinal fluid, and the like are treated. A body fluid after separating specific components in advance (e.g., plasma and serum) can be provided in the treatment.

By the way, as described above, it has been reported that use of a dialysis apparatus makes it possible to reduce an Aβ amount in the blood (Non-patent Documents 7 and 8 described above). In view of this report, in one embodiment of the Aβ removal system of the present invention, a dialysis apparatus (dialyzer) is used in combination. That is, a dialysis apparatus that is an Aβ removal means based on an action mechanism different from the Aβ removing apparatus of the present invention is incorporated to intend improvement in an Aβ removal ratio. In fact, it was confirmed that use of a dialysis apparatus in combination enables increase of an Aβ removal ratio (see examples described later).

A dialysis apparatus may be a hollow fiber type dialysis apparatus or a multilayer type (kiil type) dialysis apparatus. A material of a dialysis membrane constituting the dialysis apparatus is not particularly limited. As showing a part of examples, polyethylene resin, polystyrene resin, polysulfone resin, polyether sulfone resin, polymethyl methacrylate resin, cellulose acetate resin, and acrylonitrile-sodium methallyl sulfonate copolymer are included. Additionally, a dialysis apparatus utilizing a dialysis membrane with a large hole, which is called a high performance membrane, can also be used.

A dialysis apparatus can be connected to an Aβ removing apparatus serially or parallelly, and in the case of serial connection, a body fluid treated by the dialysis apparatus is sequentially treated by the Aβ removing apparatus, or a body fluid treated by the Aβ removing apparatus is sequentially treated by the dialysis apparatus. Use of two or more dialysis apparatuses is also possible. In this case, for example, dialysis apparatuses can be respectively arranged in front and back of an Aβ removing apparatus.

In place of a dialysis apparatus or in addition to a dialysis apparatus, an Aβ removal means using a substance having a specific binding property to Aβ may be used in combination. Typical examples of the "substance having a specific binding property to Aβ" herein include anti-Aβ antibodies (may be antibody fragments of Fab, Fab', F(ab')$_2$, scFv, dsFv antibodies), Gelsolin, and GM1 Ganglioside, and the substance is not limited thereto as long as it has a specific binding property to Aβ.

As other factors that can be included in the Aβ removal system of the present invention, a pressure meter, a flow rate detector, an abnormal action detector, in the case of a granular Aβ remover, a particulate removing filter, an air chamber and a hemolytic sensor can be exemplified.

EXAMPLES

Example 1

Evaluation of Aβ1-40 Adsorption Abilities of 6 Medical Materials (Using Simulated Plasma, Adsorption by Batch Treatment)

Figure 2:
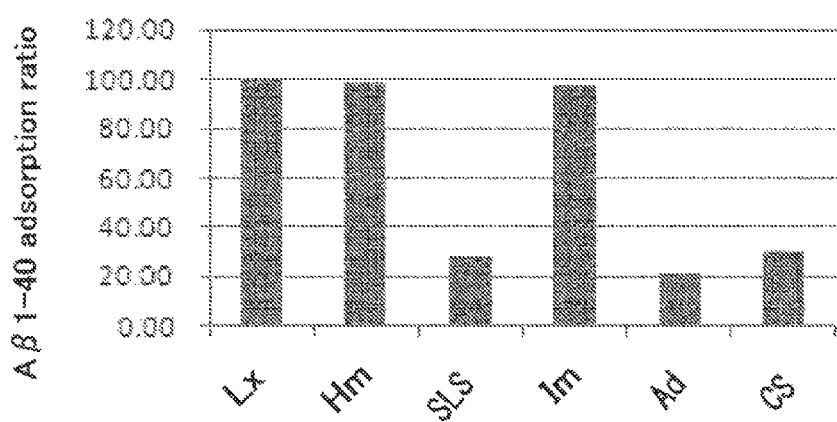
FIG. 2 is a graph showing an Aβ1-40 adsorption ability of an existing medical adsorbing material. The vertical axis shows an Aβ1-40 adsorption ratio.

750 μL of a cellulose gel bound with dextran sulfate on the surface (the sample name is referred to as "SLS", manufactured by KANEKA CORPORATION, product name: Selesorb (trade name)), 4.38 ml of petroleum pitch-based bead-like activated carbon (the sample name is referred to as "Hm", polyHEMA=hydroxy ethyl methacrylate polymer is coated on the surface in order to improve blood compatibility, manufactured by Asahi Kasei Kuraray Medical Co., Ltd., product name: Hemosorba (trade name)), 4.38 ml of a polyvinyl alcohol gel bound with tryptophan on the surface (the sample name is referred to as "Im", manufactured by Asahi Kasei Kuraray Medical Co., Ltd., product name: Immusorba (trade name)), 4.38 ml of cellulose beads bound with a hexadecy group on the surface (the sample name is referred to as "Lx", manufactured by KANEKA CORPORATION, product name: Lixelle (trade name)), 2.75 g of acetic acid cellulose beads (the sample name is referred to as "Ad", manufactured by JIMRO Co., Ltd., product name: Adacolumn (trade name)), and one sixth (64 degrees out of 360 degrees) of 1 cm-width cross-sectional polyester nonwoven fabric (the sample name is referred to as "CS", manufactured by Asahi Kasei Kuraray Medical Co., Ltd., product name: Cellsorba (trade name)) were respectively taken out from a sterilized container, charged in a 15 ml-centrifuging tube made of polypropylene (hereinafter referred to as "PP"), and washed with 10 ml of a phosphate sodium chloride buffer (hereinafter referred to as PBS(−)) three times, thereafter adding 10 ml of a PBS(−) solution with 12 ng/ml of Aβ1-40 (manufactured by Wako Pure Chemical Industries, Ltd.). One eightieth of an amount used in a column in clinical use for an adult was used as a target for an amount of each sample. In addition, 10 ml of the Aβ solution corresponds to about 1/400 of a blood amount that is clinically treated, and the Aβ concentration is set in reference to a blood Aβ concentration that increases in anti-Aβ antibody administration, which is approximately 100 times of a general blood Aβ concentration. Totally, an experiment was designed so as to increase load to each sample. To the Aβ solution, 10 mg/ml of bovine serum albumin (Wako Pure Chemical Industries, Ltd., fatty acid/globulin free, hereinafter referred to as "BSA") was added to form simulated plasma. For a control, 10 ml of a 10 mg/ml BSA/PBS(−) solution contained in the same 15 ml-centrifuging tube made of PP was used. These centrifuging tubes charged with the samples were shaken at room temperature in a dark room for 16 hours, and then an Aβ1-40 concentration was measured using an ELISA kit for Aβ1-40 measuring (manufactured by Wako Pure Chemical Industries, Ltd.) (each sample was measured after being diluted so as to be within the calibration curve range). Aβ1-40 decrease ratios (adsorption ratios) when that of the control was assumed to be 100% were sample name SLS: 28.7%, sample name Hm: 98.1%, sample name Im: 97.9%, sample name Lx: 99.1%, sample name Ad: 21.3%, and sample name CS: 30.0% (FIG. 2). Namely, Hm, Im and Lx showed high adsorption abilities.

Example 2

Evaluation of Aβ1-42 Adsorption Abilities of 6 Medical Materials (Using Simulated Plasma, Adsorption by Batch Treatment)

Figure 3:
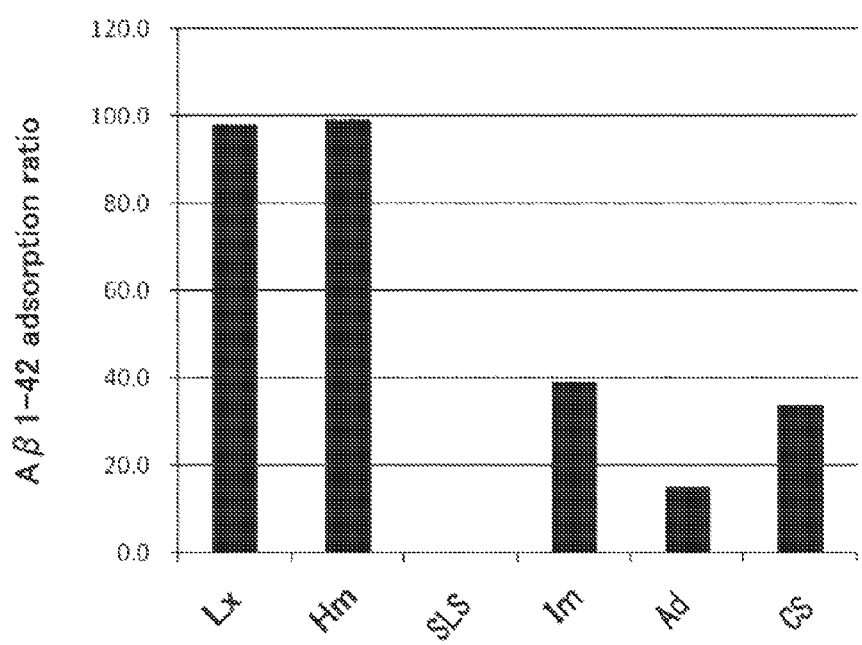
FIG. 3 is a graph showing an Aβ1-42 adsorption ability of an existing medical adsorbing material. The vertical axis shows an Aβ1-42 adsorption ratio.

An experiment was carried out in the same conditions as in Example 1 except for using 16.7 ng/ml of Aβ1-42 as an Aβ solution and an ELISA kit for Aβ1-42 measuring (manufactured by Wako Pure Chemical Industries, Ltd.) to evaluate Aβ1-42 adsorption abilities of 6 medical materials. Decrease ratios of Aβ1-42 (adsorption ratios) when that of the control after shaking for 16 hours was assumed to be 100% were sample name SLS: 0.0%, sample name Hm: 99.0%, sample name Im: 39.1%, sample name Lx: 97.7%, sample name Ad: 14.9%, and sample name CS: 33.9% (FIG. 3). Namely, Hm and Lx showed high adsorption abilities also to Aβ1-42. On the other hand, Im showed moderate adsorption ability.

Example 3

Time Lapse Evaluation of Aβ1-40 Adsorption Abilities of 3 Medical Materials (Using Simulated Plasma, Adsorption by Batch Treatment)

Figure 4:
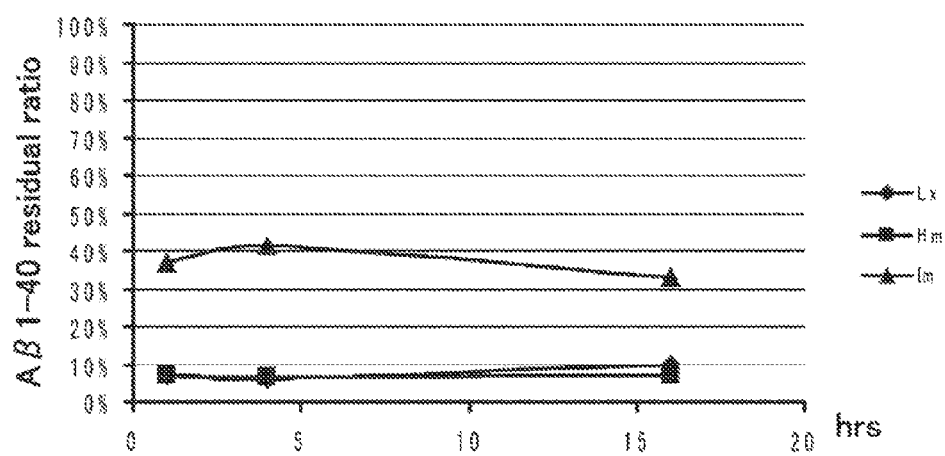
FIG. 4 is a graph showing time lapse change of an Aβ1-40 adsorption ability of an existing medical adsorbing material. The horizontal axis shows a time elapsed (hours), and the vertical axis shows an Aβ1-40 residual ratio in a solution (100−adsorption ratio (%)). Adsorption abilities were compared using simulated plasma.

Aβ1-40 adsorption abilities were measured on 3 materials of Hm, Im and Lx under room temperature at each point of shaking times of 1 hour, 4 hours, and 16 hours. The experimental conditions were in accordance with Example 1. Aβ1-40 decrease ratios (adsorption ratios) when that of the control at each time was assumed to be 100% were sample name Hm: 92.8%, sample name Im: 63.4%, and sample name Lx: 93.0% at the time point of 1 hour; sample name Hm: 93.5%, sample name Im: 58.6%, and sample name Lx: 93.9% at the time point of 4 hours; and sample name Hm: 93.0%, sample name Im: 66.8%, and sample name Lx: 90.2% at the time point of 16 hours (FIG. 4). It was found that Hm and Lx adsorb Aβ1-40 rapidly and efficiently. In addition, desorption of Aβ1-40 after adsorption was not observed.

Example 4

Time Lapse Evaluation of Aβ1-42 Adsorption Abilities of 3 Medical Materials (Using Simulated Plasma, Adsorption by Batch Treatment)

Figure 5:
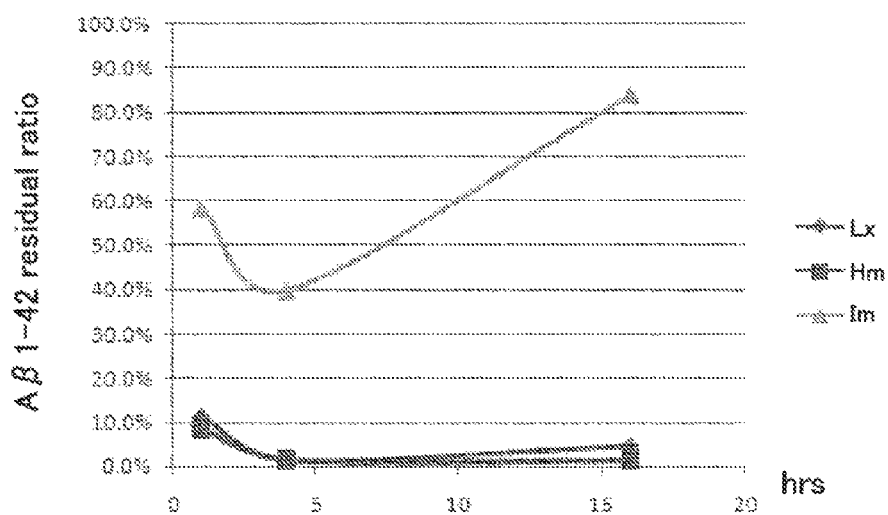
FIG. 5 is a graph showing time lapse change of an Aβ1-42 adsorption ability of an existing medical adsorbing material. The horizontal axis shows a time elapsed (hours), and the vertical axis shows an Aβ1-42 residual ratio in a solution (100−adsorption ratio (%)). Adsorption abilities were compared using simulated plasma.

Aβ1-42 adsorption abilities were measured on 3 materials of Hm, Im and Lx under room temperature at each point of shaking times of 1 hour, 4 hours, and 16 hours. The experimental conditions were in accordance with Example 2. Aβ1-42 decrease ratios (adsorption ratios) when that of the control at each time was assumed to be 100% were sample name Hm: 91.6%, sample name Im: 41.5%, and sample name Lx: 88.7% at the time point of 1 hour; sample name Hm: 98.4%, sample name Im: 60.1%, and sample name Lx: 98.5% at the time point of 4 hours; and sample name Hm: 98.6%, sample name Im: 16.0%, and sample name Lx: 95.3% at the time point of 16 hours (FIG. 5). It was found that Hm and Lx adsorb Aβ1-42 rapidly and efficiently. In addition, desorption of Aβ1-42 after adsorption was not observed.

Example 5

Time Lapse Evaluation of Aβ1-40 Adsorption Abilities of 3 Medical Materials (Using Human Plasma, Adsorption by Batch Treatment)

Figure 6:
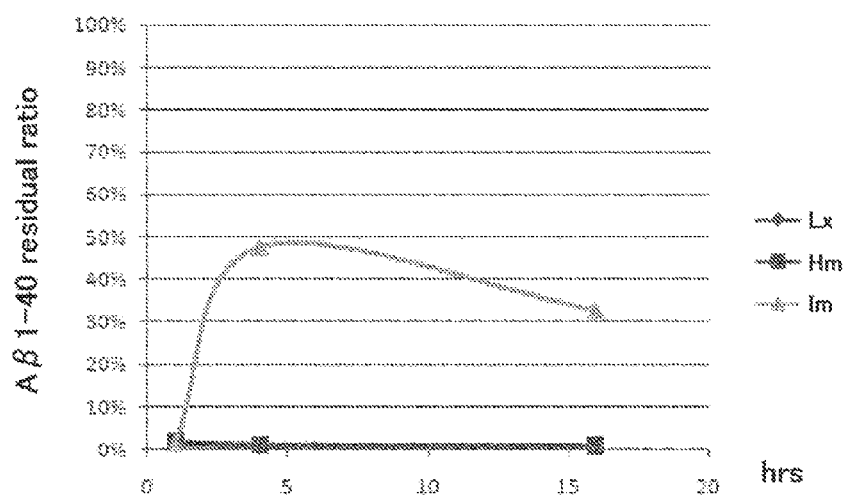
FIG. 6 is a graph showing time lapse change of an Aβ1-40 adsorption ability of an existing medical adsorbing material. The horizontal axis shows a time elapsed (hours), and the vertical axis shows an Aβ1-40 residual ratio in a solution (100−adsorption ratio (%)). Adsorption abilities were compared using human fresh frozen plasma (FFP).

An operation of recovering human fresh frozen plasma (hereinafter referred to as FFP), which slightly remained in a bag used for plasma exchange, was repeated to collect FFP. Aβ1-40 adsorption abilities were measured on 3 materials of Hm, Im and Lx under room temperature at each point of shaking times of 4 hours and 16 hours, using the FFP thus collected in place of a 10 mg/ml BSA/PBS(−) solution. When an adsorption experiment was carried out, Aβ1-40 peptide was added to this FFP to adjust a final concentration at 22.0 ng/ml that was approximately 100 times. The experimental conditions were in accordance with Example 1. Aβ1-40 decrease ratios (adsorption ratios) when that of the control at each time was assumed to be 100% were sample name Hm: 98.3%, sample name Im: 98.5%, and sample name Lx: 98.5% at the time point of 1 hour; sample name Hm: 99.0%, sample name Im: 52.5%, and sample name Lx: 99.1% at the time point of 4 hours; and sample name Hm: 99.2%, sample name Im: 67.3%, and sample name Lx: 99.2% at the time point of 16 hours (FIG. 6). It was thus found that Hm and Lx adsorb Aβ1-40 rapidly and efficiently also in the case of using human plasma. Desorption of Aβ1-40 after adsorption was not observed.

Example 6

Time Lapse Evaluation of Aβ1-42 Adsorption Abilities of 3 Medical Materials (Using Human Plasma, Adsorption by Batch Treatment)

Figure 7:
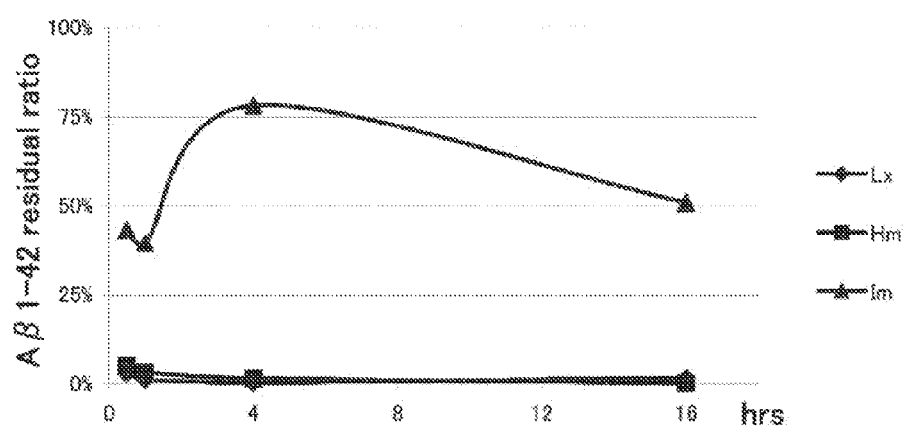
FIG. 7 is a graph showing time lapse change of an Aβ1-42 adsorption ability of an existing medical adsorbing material. The horizontal axis shows a time elapsed (hours), and the vertical axis shows an Aβ1-42 residual ratio in a solution (100−adsorption ratio (%)). Adsorption abilities were compared using human fresh frozen plasma (FFP).

Aβ1-42 adsorption abilities were measured on 3 materials of Hm, Im and Lx under room temperature at each point of shaking times of 0.5 hour, 1 hour and 16 hours, using FFP collected in the same manner as in Example 5 in place of a 10 mg/ml BSA/PBS(−) solution. The concentration of Aβ1-42/FFP brought into contact with an adsorbing material was 23.8 ng/ml, which was approximately 1000 times as high as the Aβ1-42 concentration of FFP itself of 23.4 pg/ml. The experimental conditions were in accordance with Example 2. Aβ1-42 decrease ratios (adsorption ratios) when that of the control at each time was assumed to be 100% were sample name Hm: 94.8%, sample name Im: 56.8%, and sample name Lx: 97.2% at the time point of 0.5 hour; sample name Hm: 96.9%, sample name Im: 60.5%, and sample name Lx: 98.9% at the time point of 1 hour; sample name Hm: 98.5%, sample name Im: 21.8%, and sample name Lx: 99.7% at the time point of 4 hours; and sample name Hm: 99.9%, sample name Im: 49.1%, and sample name Lx: 98.4% at the time point of 16 hours (FIG. 7). It was thus found that Hm and Lx adsorb Aβ1-42 rapidly and efficiently also in the case of using human plasma. Desorption of Aβ1-42 after adsorption was not observed.

Example 7

Evaluation of Aβ1-40 Adsorption Abilities of 3 Medical Materials (Using Simulated Plasma, Adsorption by Continuous Treatment)

Figure 8:
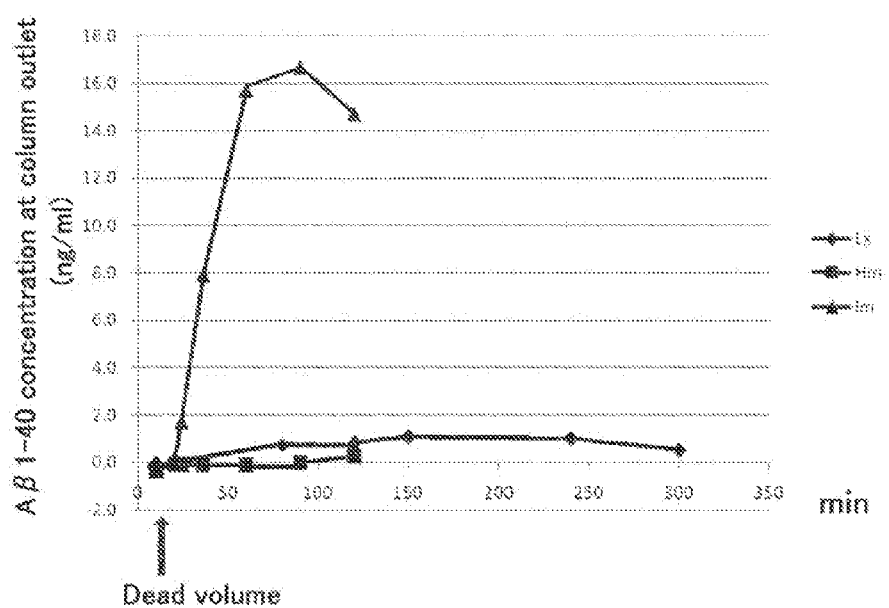
FIG. 8 is a graph showing an Aβ1-40 adsorption ability of an existing medical adsorbing material (in the case where simulated plasma was continuously treated). The horizontal axis shows a time elapsed (minutes), and the vertical axis shows an Aβ1-40 concentration at a column outlet (ng/ml). Lx: Lixelle, Hm: Hemosorba, Im: Immusorba.

A material to be evaluated was filled in a 2.5 mL-cylindrical miniature column (a column size for an adsorbing material portion in the case of the sample name Lx is 9 mm in diameter and 30 mm in length), and a 10 mg/mL BSA/PBS(−) solution was primed with a perista pump at a flow rate of 10 ml/hr for 90 minutes. Then, a liquid flown to the material was converted to a 10 mg/ml BSA/PBS(−) solution containing Aβ1-40 at about 30 ng/ml being the same as Example 1, and the solution was passed through the material at the same flow rate for 120 minutes (sample name Hm and sample name Im) or 300 minutes (sample name Lx). An Aβ1-40 concentration in the liquid after passing through the material was measured in the same manner as in Example 1. This system assumes 1/200 of a human clinical application and simulates treating 4 L of plasma in 2 hours. Measurement results are shown in FIG. 8. The adsorption ability to Aβ1-40 was Im<Hm<Lx. Lx and Hm showed sufficient adsorption abilities event to Aβ at an about 100 times higher concentration than an actual blood Aβ concentration.

Example 8

Evaluation of Aβ1-42 Adsorption Abilities of 2 Medical Materials (Using Simulated Plasma, Adsorption by Continuous Treatment)

Figure 9:
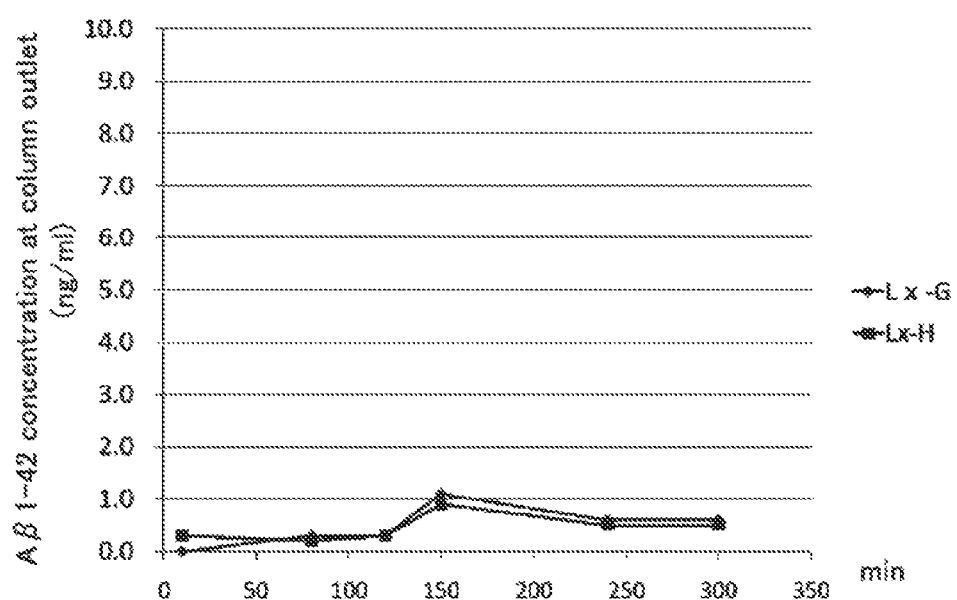
FIG. 9 is a graph showing an Aβ1-42 adsorption ability of an existing medical adsorbing material (in the case where simulated plasma was continuously treated). The horizontal axis shows a time elapsed (minutes), and the vertical axis shows an Aβ1-42 concentration at a column outlet (ng/ml). Lx: Lixelle.
Figure 10:
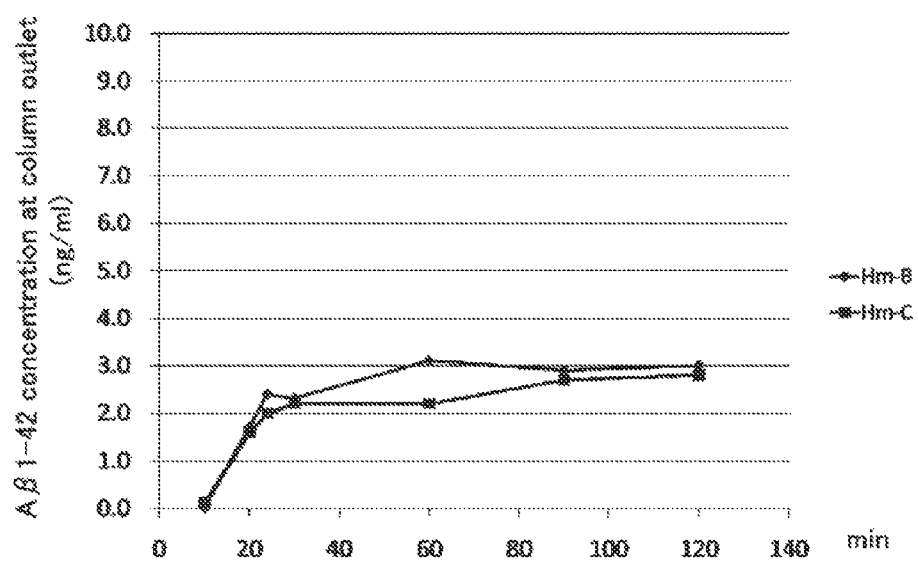
FIG. 10 is a graph showing an Aβ1-42 adsorption ability of an existing medical adsorbing material (in the case where simulated plasma was continuously treated). The horizontal axis shows a time elapsed (minutes), and the vertical axis shows an Aβ1-42 concentration at a column outlet (ng/ml). Hm: Hemosorba.

A material to be evaluated was filled in a 2.5 mL-cylindrical miniature column (a column size for an adsorbing material portion in the case of the sample name Lx is 9 mm in diameter and 30 mm in length), and a 10 mg/mL BSA/PBS(–) solution was primed with a perista pump at a flow rate of 10 ml/hr for 90 minutes. A liquid flown to the material was then converted to a 10 mg/ml BSA/PBS(–) solution containing Aβ1-42 at about 30 ng/ml being the same as Example 2, and the solution was passed through the material at the same flow rate for 120 minutes (sample name Hm) or 300 minutes (sample name Lx). An Aβ1-42 concentration in the liquid after passing through the material was measured in the same manner as in Example 2. This system assumes 1/200 of a human clinical application and simulates treating 4 L of plasma in 2 hours. The measurement results of two experiments on the sample name Lx (Lx-G, Lx-H) are shown in FIG. 9, and the measurement results of two experiments on the sample name Hm (Hm-B, Hm-C) are shown in FIG. 10. Lx and Hm showed sufficient adsorption abilities event to Aβ at an about 100 times higher concentration than an actual blood Aβ concentration.

Example 9

Evaluation of Aβ1-40 Adsorption Abilities of Materials with Different Lengths of Alkyl Chains (Using Simulated Plasma, Adsorption by Batch Treatment)

Figure 11:
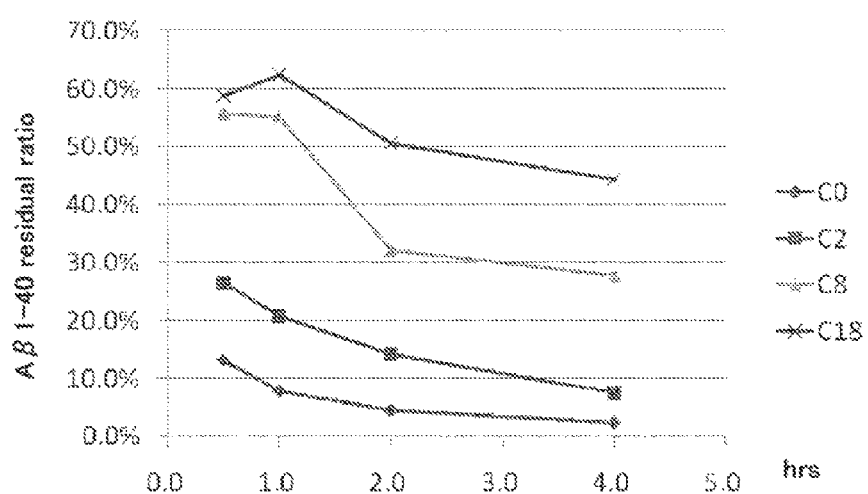
FIG. 11 is a graph showing an Aβ1-40 adsorption ability of a silica carrier having a linear alkyl chain on the surface. The horizontal axis shows a time elapsed (hours), and the vertical axis shows an Aβ1-40 residual ratio in a solution (100−adsorption ratio (%)). The relationship between the length of the linear alkyl chain and the adsorption ability was examined in comparison using simulated plasma. Carbon contents of respective samples are C0: 0%, C2: 5.5%, C8: 12%, and C18: 19%.

A plurality of silica gel carriers having linear alkyl groups with the different numbers of carbon atoms, which are present on the surfaces thereof, were prepared to comparatively examine Aβ1-40 adsorption abilities. The measurement of the adsorption abilities was the same as in Example 1 and Example 3. For materials, only a carrier of InertSep FF manufactured by GL Sciences Inc. (bead diameter 120 μm, pore diameter 6 nm, specific surface area 450 m$^2$/g, pore volume 0.7 ml/g) (sample name C0), a carrier having an ethyl group (sample name C2), a carrier having an octyl group (sample name C8), and a carrier having an octadecyl group (sample name C18) were used. Note that respective carbon contents were C0: carbon content 0%, C2: carbon content 5.5%, C8: carbon content 12%, and C18: carbon content 19%. Aβ1-40 decrease ratios (adsorption ratios) when that of the control at each time was assumed to be 100% were measured under room temperature at each point of shaking times of 0.5 hour, 1 hour and 4 hours. As a length of an alkyl chain on the surface is shorter (that is, hydrophobicity becomes weak), an Aβ1-40 adsorption ability is higher (FIG. 11). In addition, the maximum adsorption ability was shown in the case where no alkyl chain on the surface exists.

Example 10

Evaluation of Aβ1-40 Adsorption Ability of Cellulose Carrier (Using Simulated Plasma, Adsorption by Batch Treatment)

Figure 12:
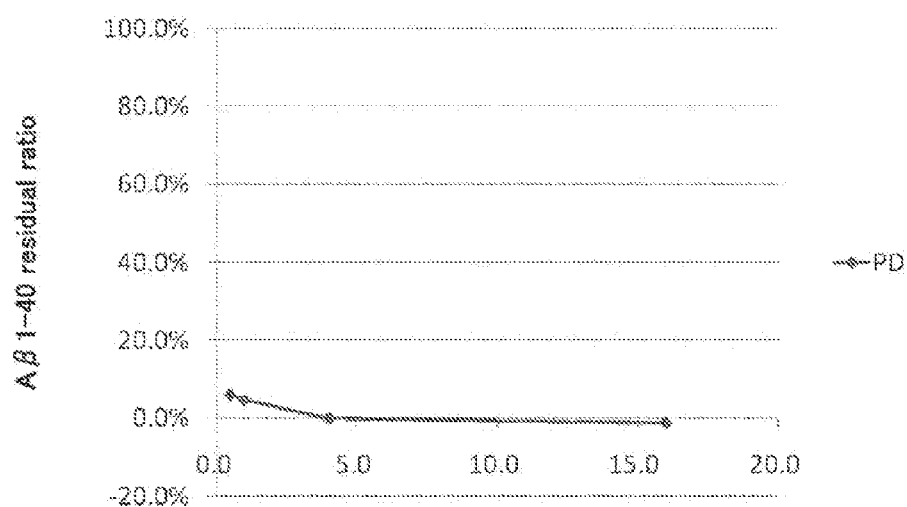
FIG. 12 is a graph showing an Aβ1-40 adsorption ability of a cellulose carrier. The horizontal axis shows a time elapsed (hours), and the vertical axis shows an Aβ1-40 residual ratio in a solution (100−adsorption ratio (%)).

An Aβ1-40 adsorption ability of a cellulose carrier without having a linear alkyl chain on the surface was measured according to Example 1 and Example 3. For a material, Viscopearl-mini PD4002 manufactured by Rengo Co., Ltd. (bead diameter 400 μm, specific surface area 1 to 10 m$^2$/g) was used. Aβ1-40 decrease ratios (adsorption ratios) measured under room temperature at each point of shaking times of 0.5 hour, 1 hour, 4 hours and 16 hours when that of the control at each time was assumed to be 100% were 93.7%, 95.3%, 100.0%, and 101.1%, respectively (FIG. 12). As described above, a cellulose bead that is a hydrophilic carrier also showed a significantly excellent Aβ adsorption ability.

Example 11

Change in Blood Aβ Concentrations when Lx is Applied to Human Dialysis Patient

Figure 13:
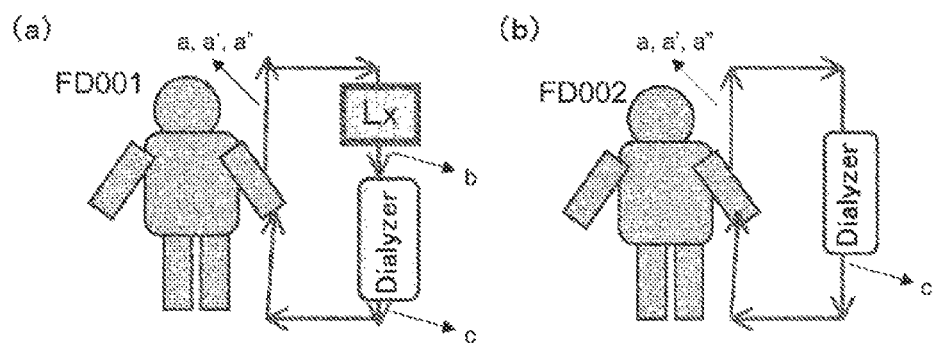
FIG. 13 shows an overview of a blood purification experiment. (a) A column filled with Lx (Lixelle) and a dialysis apparatus were serially connected and the blood was circulated. (b) A dialysis apparatus was solely used (comparative example).

A blood purification column of Lx (Lixelle S-15, KANEKA CORPORATION) and a dialyzer (made of PMMA, TORAY MEDICAL Co., Ltd.) were serially connected in this order from the blood removal side (FIG. 13(a)), to carry out blood purification by extracorporeal circulation of a renal failure patient (purification with sample name Lx and dialysis treatment) for 4 hours. Patient's blood just before the beginning of the dialysis session, and Patient's blood at the inlet and the outlet of the column containing the sample name Lx at 1 hour after the beginning of the dialysis session, and patient's blood at the dialyzer outlet at the same time point, and patient's blood at completion of the dialysis were collected, and blood Aβ1-40 concentrations were measured in the same manner as in Example 1. As a result, Aβ1-40 in the patient's blood before initiation of the dialysis was about 596 pg/ml, Aβ1-40 in the inlet of the column for the sample name Lx at 1 hour after initiation of the dialysis (this concentration can be regarded as the same concentration as the blood circulated in the patient's body) was about 334 pg/ml, Aβ1-40 in the outlet of the column for the sample name Lx (that is also the inlet of the dialyzer) was about 170 pg/ml, Aβ1-40 in the dialyzer outlet was about 90 pg/ml, and Aβ1-40 in the patient's blood at completion of the dialysis was about 350 pg/ml (FIG. 14). An Aβ concentration decrease ratio of the patient's circulating blood before and after the dialysis was 41.3%, an Aβ removal ratio before and after the column for the sample name Lx was 49.0%, and an Aβ concentration decrease ratio of the patient's circulating blood at 1 hour after initiation of the dialysis was 44% (upper column in FIG. 15). As described above, Lx was able to efficiently remove Aβ. Also, combination use of a dialysis apparatus made it possible to improve an Aβ removal ratio.

Comparative Example 1

Change in Blood Aβ Concentrations when Only Dialysis was Performed without Lx (Dialysis Patient Who is not Affected by Alzheimer's Disease)

A dialysis treatment was carried out with a dialyzer (made of PMMA, TORAY MEDICAL Co., Ltd.) in the same manner as in Example 10 (different patient from the patient in Example 10) except for not using a blood purification column of Lx (Lixelle S-15, KANEKA CORPORATION). The patient's blood was collected before initiation of the dialysis, at 1 hour after initiation of the dialysis, and at completion of the dialysis to measure blood Aβ1-40 concentrations in the same manner as in Example 1. The results showed that the blood Aβ1-40 concentration before initiation of the dialysis was about 527 pg/ml, the blood Aβ1-40 concentration at 1 hour after initiation of the dialysis was about 435 pg/ml, and the blood Aβ1-40 concentration at completion of the dialysis was about 396 pg/ml (FIG. 16). The Aβ concentration decrease ratio of the patient's circulating blood before and after the dialysis was 25.0%, the Aβ concentration decrease ratio of the patient's circulating blood at 1 hour after initiation of the dialysis was 17.5% (lower column in FIG. 15), and the Aβ decrease ratios were significantly lowered as compared to the case where an Lx column and a dialysis apparatus were used in combination (Example 11).

Example 12

Change in Blood Aβ Concentrations when Lx was Applied to Two Human Dialysis Patients The blood purification of 4 hours was carried out on two renal failure patients (referred to as patient A and patient B) in the same method as in Example 11 (provided that a dialysis apparatus made of PS (Asahi Kasei Kuraray Medical Co., Ltd.) was used). The patient's blood before initiation of the dialysis, and the patient's blood in the inlet and the outlet of the column for the sample name Lx at 1 hour and 4 hours after initiation of the dialysis were collected, to measure blood Aβ1-40 concentrations and blood Aβ1-42 concentrations in the same manner as in Example 1 and Example 2. The results were shown in FIG. 17. Aβ1-40 concentration decrease ratios of the patient's circulating blood before and after the dialysis were patient A; 51.8%, patient B; 43.9%, and Aβ1-42 concentration decrease ratios were patient A; 43.3% and patient B; 34.4%. Namely, similarly to Example 11, Aβ1-40 and Aβ1-42 were able to be efficiently removed by Lx also in other two patients.

Example 13

Evaluation of Aβ Removal Abilities of Materials with Different Lengths of Alkyl Chains 40 ng/ml of Aβ (Aβ1-40 or Aβ1-42) in a 10 mg/ml BSA/PBS(−) solution was treated with cellulose beads having a linear alkyl chain of a certain length (C0, C2, C4, C8, C16 or C22) or silica beads having a linear alkyl chain of a certain length (C0, C2, C8 or C18) by shaking at room temperature (batch treatment). Aβ concentration of the solution was measured by ELISA at each point of shaking times of 0.5 hour, 1 hour, 2 hours and 4 hours. For a control, an Aβ solution contained in a tube made of PP, which was subjected to the same treatment except the addition of the beads, was used. The results were shown in Table 1 (removal ratio of Aβ1-40 by Cellulose beads), Table 2 (removal ratio of Aβ1-42 by Cellulose beads), FIG. 18 and FIG. 19.

TABLE 1

Removal ratio of Aβ1-40 by Cellulose beads

| | hr | | | |
|---|---|---|---|---|
| | 0.5 | 1 | 2 | 4 |
| C0 | 16.3% | 10.0% | 7.8% | 9.9% |
| C2 | 18.6% | 12.0% | 7.6% | 11.9% |
| C4 | 21.5% | 15.7% | 13.0% | 22.5% |
| C8 | 39.1% | 36.5% | 30.4% | 46.1% |
| C16 | 99.8% | 99.8% | 99.1% | 99.5% |
| C22 | 99.7% | 99.8% | 99.7% | 99.6% |

TABLE 2

Removal ratio of Aβ1-42 by Cellulose beads

| | hr | | | |
|---|---|---|---|---|
| | 0.5 | 1 | 2 | 4 |
| C0 | 6.7% | 9.4% | 11.0% | 17.0% |
| C2 | 3.9% | 3.7% | 12.8% | 21.8% |
| C4 | 8.1% | 8.4% | 20.5% | 24.3% |
| C8 | 47.5% | 48.7% | 51.7% | 55.1% |
| C16 | 99.9% | 99.7% | 99.9% | 99.8% |
| C22 | 99.9% | 99.9% | 99.6% | 99.4% |

Figure 18:
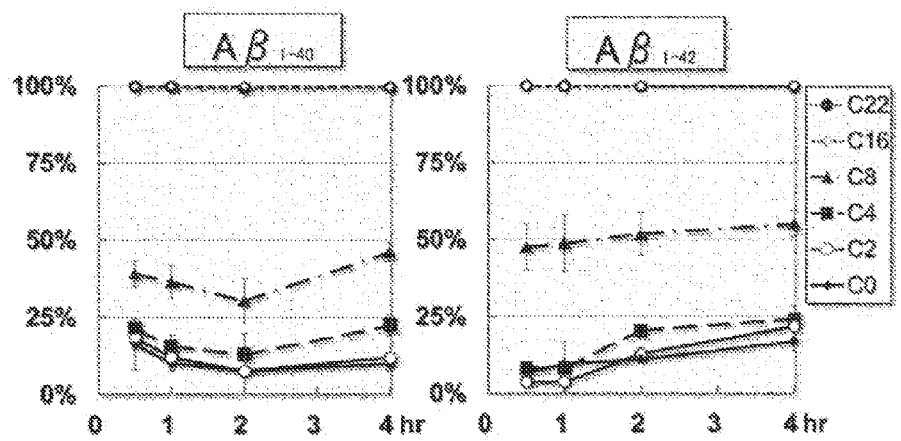
FIG. 18 is graphs showing a removal ratio of Aβ1-40 (left) or Aβ1-42 (right). Cellulose beads having a linear alkyl chain (C0. C2, C4, C8, C16 or C22) on the surface were used as Aβ adsorbents. The horizontal axis shows a time elapsed (hours).
Figure 19:
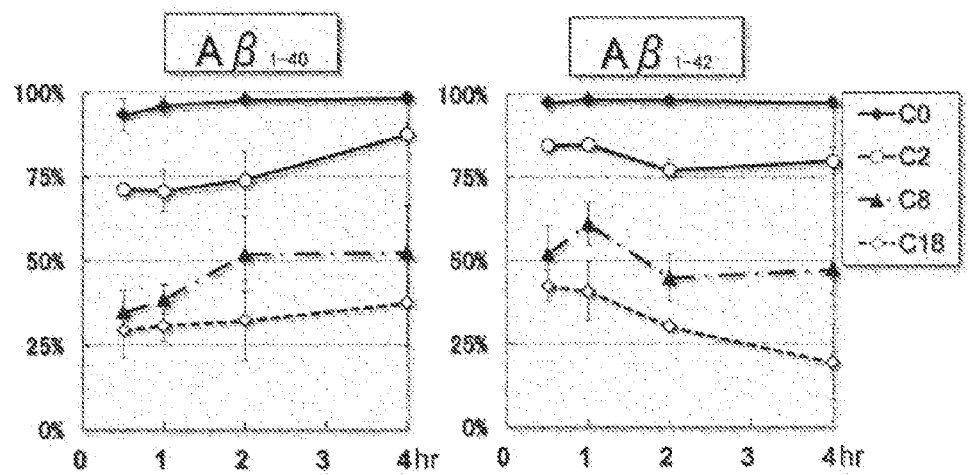
FIG. 19 is graphs showing a removal ratio of Aβ1-40 (left) or Aβ1-42 (right). Silica beads having a linear alkyl chain (C0. C2, C8 or C18) on the surface were used as Aβ adsorbents. The horizontal axis shows a time elapsed (hours).
Figure 20:
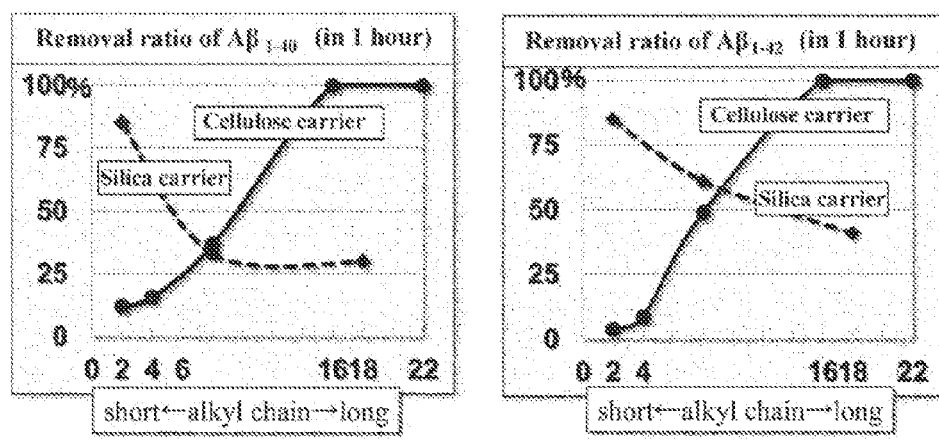
FIG. 20 shows a relationship between the removal ratio of Aβ1-40 (left) or Aβ1-42 (right) and the length of alkyl chain for both cellulose and silica carriers.

As shown in the Tables and FIG. 18, the Aβ removal ratios of cellulose beads after 4 hours of shaking are: 9.9% (Aβ1-40) and 17.0% (Aβ1-42) for C0; 99.6% (Aβ1-40) and 99.4% (Aβ1-42) for C22. Meanwhile, as shown in FIG. 19, the Aβ removal ratios of silica beads after 4 hours of shaking are: 98.6% (Aβ1-40) and 97.5% (Aβ1-42) for C0; 40.0% (Aβ1-40) and 19.6% (Aβ1-42) for C18. Interesting relationships are observed between the removal ratio of Aβ and the length of alkyl chain (FIG. 20) for both cellulose and silica carriers.
Industrial Applicability The Aβ remover of the present invention is excellent in Aβ removal ability. According to an extracorporeal circulation system into which the Aβ remover of the invention is incorporated, a therapeutic or preventive method for Alzheimer's disease, which has less side effects, attains prompt effects, and is also inexpensively practicable, can be achieved.

The invention is not limited at all to the above described embodiments of the invention and description of examples. Various modified embodiments are also included in the invention within a range where a skilled person can easily conceive without deviating from the scope of claims of the patent. Contents of articles, unexamined patent applications, and patent applications expressed in the present specification are incorporated herein by reference to the whole contents thereof.

What is claimed is:
1. A method of removing amyloid β protein, comprising:
identifying a patient in need of removal of amyloid β protein; and
contacting a body fluid of said patient with a composition including a carrier made of any one material selected from the group consisting of cellulose and silica, wherein the carrier is unmodified or has an alkyl chain having 1 to 22 carbon atoms on the surface thereof.
2. The method according to claim 1, wherein the carrier is made of silica and has the alkyl chain on the surface thereof, the alkyl chain being bound to the carrier via a silanol group (SiOH).
3. The method according to claim 2, wherein the number of carbon atoms is 1 to 5.
4. The method according to claim 2, wherein the number of carbon atoms is 1 to 2.
5. The method according to claim 1, wherein the carrier is made of silica and is unmodified.
6. The method according to claim 1,
wherein the carrier is made of cellulose, and
wherein the carrier has the alkyl chain having 1 to 22 carbon atoms on the surface thereof.
7. The method according to claim 1, wherein the carrier is made of cellulose and is unmodified.
8. A method of removing amyloid β protein, comprising:
identifying a patient in need of removal of amyloid β protein; and contacting a body fluid of said patient with a composition including a carrier made of activated carbon,
wherein the surface of the carrier is covered with a hydrophilic polymer.

9. The method according to claim 8, wherein the hydrophilic polymer is a polymer of methacrylic acid 2-hydroxyethyl ester (pHEMA).

10. A method of removing amyloid β protein, comprising:
identifying a patient in need of removal of amyloid β protein; and
contacting a body fluid of said patient with a composition including a carrier made of polyvinyl alcohol and having tryptophan on the surface thereof, and
measuring an amount of amyloid β protein in the body fluid of said patient before contacting the body fluid of said patient with the composition including the carrier made of polyvinyl alcohol and having tryptophan on the surface thereof.

\* \* \* \* \*